(12) United States Patent
Sun

(10) Patent No.: US 10,351,495 B2
(45) Date of Patent: Jul. 16, 2019

(54) CONVERSION OF CHLOROFLUOROROPANES AND CHLOROFLUROPROPENES TO MORE DESIRABLE FLUOROPROPANES AND FLUOROROPENES

(71) Applicant: THE CHEMOURS COMPANY FC, LLC, Wilmington, DE (US)

(72) Inventor: Xuehui Sun, Kennett Square, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 15/786,199

(22) Filed: Oct. 17, 2017

(65) Prior Publication Data

US 2018/0037525 A1 Feb. 8, 2018

Related U.S. Application Data

(63) Continuation of application No. 15/466,148, filed on Mar. 22, 2017, now Pat. No. 9,822,047, which is a continuation of application No. 14/680,092, filed on Apr. 7, 2015, now Pat. No. 9,637,429.

(60) Provisional application No. 61/980,157, filed on Apr. 16, 2014.

(51) Int. Cl.
| | |
|---|---|
| *C07C 21/18* | (2006.01) |
| *C07C 19/10* | (2006.01) |
| *C07C 17/354* | (2006.01) |
| *C07C 17/25* | (2006.01) |
| *C07C 17/23* | (2006.01) |

(52) U.S. Cl.
CPC ............ *C07C 17/354* (2013.01); *C07C 17/23* (2013.01); *C07C 17/25* (2013.01)

(58) Field of Classification Search
CPC .................................................... C07C 21/18
See application file for complete search history.

(56) References Cited

U.S. PATENT DOCUMENTS

| | | | |
|---|---|---|---|
| 7,335,804 B2 | 2/2008 | Nair et al. | |
| 7,872,161 B2 * | 1/2011 | Rao | .......................... C07C 17/23 570/156 |
| 7,906,693 B2 * | 3/2011 | Nappa | ..................... C07C 17/23 570/124 |
| 7,981,312 B2 * | 7/2011 | Nappa | ..................... C07C 17/23 252/67 |
| 8,357,828 B2 | 1/2013 | Okamoto et al. | |
| 8,399,722 B2 | 3/2013 | Kawaguchi et al. | |
| 8,530,710 B2 | 9/2013 | Takagi et al. | |
| 8,530,711 B2 | 9/2013 | Kawaguchi et al. | |
| 8,569,553 B2 | 10/2013 | Takagi et al. | |
| 8,766,021 B2 | 7/2014 | Kawaguchi et al. | |
| 2010/0022808 A1 | 1/2010 | Rao et al. | |
| 2010/0185028 A1 | 7/2010 | Okamoto | |
| 2010/0204529 A1 | 8/2010 | Terada et al. | |
| 2012/0108859 A1 | 5/2012 | Nappa et al. | |
| 2014/0305161 A1 * | 10/2014 | Kawaguchi | ........... C07C 17/383 62/617 |

FOREIGN PATENT DOCUMENTS

| | | |
|---|---|---|
| CN | 10229552 A | 5/2011 |
| EP | 0 687 659 A1 | 12/1995 |
| JP | 2010047571 A | 3/2010 |
| WO | 2007/056128 A1 | 5/2007 |
| WO | 2010/013576 A1 | 2/2010 |
| WO | 2010082662 A1 | 7/2010 |
| WO | 2012/061022 A2 | 5/2012 |
| WO | WO-2013099856 A1 * | 7/2013 ........... C07C 17/383 |

OTHER PUBLICATIONS

Satterfield, Charles N. Heterogeneous Catalysis in Industrial Practice, Catalyst Preparation and Manufacture, 1991, pp. 87-112, 2$^{nd}$ ed., McGraw-Hill, New York, NY.
Augustine, R. L. Marcel Dekker, Inc., 1965, pp. 863-864, 95 Madison Ave., New York, NY.
Takahashi, K., et al., Patent No. JP2010047571A; Published Mar. 4, 2010; English translation; pp. 1-20.

* cited by examiner

*Primary Examiner* — Medhanit W Bahta

(57) ABSTRACT

A process is provided comprising contacting and reacting the compound $CF_3CF_2CHXCl$, wherein X is H or Cl, or the compound $CF_3CF{=}CXCl$, wherein X is H or Cl, with hydrogen in the presence of a catalyst consisting essentially of Cu, Ru, Cu—Pd, Ni—Cu, and Ni—Pd, to obtain as a result thereof reaction product comprising hydrofluoropropenes or intermediates convertible to said hydrofluoropropenes, notably $CF_3CF{=}CH_2$ and $CF_3CH{=}CHF$.

5 Claims, No Drawings

CONVERSION OF CHLOROFLUOROROPANES AND CHLOROFLURUOPROPENES TO MORE DESIRABLE FLUOROPROPANES AND FLUOROROPENES

FIELD OF THE INVENTION

The present invention relates to chemical processes for converting chlorofluoropropanes (HCFC) and chlorofluoropropenes (CFO) to more desirable fluoropropanes and fluoropropenes, especially propenes that are hydrofluoroolefins (HFO), i.e. free of Cl, and to intermediates from which these HFOs can be obtained.

BACKGROUND OF THE INVENTION

U.S. Pat. No. 8,399,722 discloses the hydrogenation of at least one of 1,1-dichloro-2,3,3,3-tetrafluoropropene ($CF_3CF=Cl_2$, 1214ya) and 1-chloro-2,3,3,3-tetrafluoropropene ($CF_3CF=CHCl$, 1224yd) in the presence of catalyst composed of Pd supported on a carbon carrier to obtain 2,3,3,3-tetrafluoropropene ($CF_3CF=CH_2$, 1234yf), which is free of chlorine and which has promise at least as a refrigerant exhibiting both low ozone depletion potential and low global warming potential. Example 2 discloses the conversion rate 1214ya to 1234yf to be 75%, which can also be considered the selectivity of the process. In Example 3 the selectivity dropped to 69%.

Processes are desired to obtain better results in the production of HFO-1234yf, and/or to obtain HFO-1234ze ($CF_3CH=CHF$), 1,3,3,3-tetrafluoropropene), which is also free of chlorine and has refrigerant application, and/or which opens up new routes for obtaining desirable HFOs such as HFO-1234yf or HFO-1234ze.

SUMMARY OF THE INVENTION

The present invention provides the process comprising contacting and reacting the compound $CF_3CF_2CHXCl$, wherein X is H or Cl, or the compound $CF_3CF=CXCl$, wherein X is H or Cl, with hydrogen in the presence of a catalyst consisting essentially Cu, Ru, Cu—Pd, Ni—Cu, and Ni—Pd, to obtain as a result thereof reaction product comprising hydrofluoropropenes or intermediates convertible to said hydrofluoropropenes. When in the compound $CF_3CF_2CHXCl$, X is H, then the compound is HCFC-235cb, and when Cl, the compound is HCFC-225ca. When in the compound $CF_3CF=CXCl$, X is H, the compound is HCFO-1224yd, and when X is Cl, the compound is CFO-1214ya. These are the reactant compounds in this Hydrogenation Process.

Another embodiment of the present invention is the Intermediates Process, i.e. the process for converting the intermediates obtained in the Hydrogenation Process to the desired hydrofluoropropenes. The Intermediates Process comprises such reactions as hydrogenation, dehydrochlorination, and dehydrofluorination. The catalysts used in the Hydrogenation Process are preferably those used in the hydrogenation reactions in the Intermediates Process.

The desired hydrofluoropropenes include HFO-1234yf ($CF_3CF=CH_2$), HFO-1234ze ($CF_3CH=CHF$), and HFO-1225zc ($CF_3CH=CF_2$).

Reaction pathways (reactant/reaction product) included in the Hydrogenation Process and Intermediates Process are as follows:

When the reactant compound is HCFC-225ca, the reaction product comprises HFO-1234yf ($CF_2CF=CH_2$). The reaction product may also comprise at least one of HCFO-1224yd, and HCFC-235cb ($CF_3CF_2CH_2Cl$) which are intermediates through which HFO-1234yf can be obtained. HCFO-1224yd can be converted directly to HFO-1234yf. HCFC-235cb can be converted indirectly to HFO-1234yf by first being converted to HCFO-1224yd, which is then converted to HFO-1234yf. The HCFC-235cb can also be converted directly to HFO-1234yf, i.e. the reaction product of hydrogenating HCFC-235cb comprises HFO-1234yf. This direct conversion can result when the HCFC-235cb is the reactant compound $CF_3CF_2CHXCl$, wherein X is H.

Typically, the reactant compound HCFC-225ca will be mixed with HCFC-225aa ($CF_3CCl_2CHF_2$), whereby the HCFC-225aa will accompany the HCFC-225ca in the contacting and reacting step. The resultant hydrogenation of the HCFC-225aa forms the reaction product comprising at least one of HCFO-1224xe ($CF_3CCl=CHF$), HCFC-235da ($CF_3CHClCHF_2$), and HCFC-245fa ($CF_3CH_2CF_2H$), which are intermediates in the formation of HFO-1234ze ($CF_3CH=CHF$). The hydrogenation of HCFC-225aa can also form HFO-1234ze directly.

When the intermediate is HCFO-1234xe, the reaction pathway to HFO-1234ze is to first form HCFC-23db ($CF_3CHClCH_2F$), which can be converted to HFO-1234ze or 1234ze can be formed directly from 1234xe. When the intermediate is HCFC-235da, this can be converted to HFO-1234ze. When the intermediate is HCFC-245fa, it can be converted to HFO-1234ze directly.

When the reactant compound is either CFO-1214ya or 1224yd or a mixture thereof, the reaction product comprises HFO-1234yf.

DETAILED DESCRIPTION OF THE INVENTION

The hydrogenation reactions of the present invention (Hydrogenation Process and Intermediates Process) are preferably carried out in the gas phase in a corrosion-resistance reactor packed with a catalytically effective amount of the catalyst at temperatures and pressures and contact times effective to produce the reaction result desired for the particular reaction. The hydrogenation reactions are preferably carried out at atmospheric pressure or at higher or lower pressures.

The hydrogenation catalyst in each hydrogenation reaction in the Hydrogenation Process consists essentially or Cu, Ru, Cu—Pd, Ni—Cu, or Ni—Pd, with or without a support (carrier). These same catalysts are preferably used in the hydrogenation reactions in the Intermediates Process, although the catalyst used in a particular hydrogenation reaction in the Intermediates Process can be different from the catalyst used in a hydrogenation reaction in the Hydrogenation Process. The catalyst can include a support in each of the hydrogenation reactions. When a support is used as part of the catalyst, the Cu, Ru, Cu—Pd, Ni—Cu, or Ni—Pd can be loaded onto the support in a conventional manner used for loading metals onto supports, including combinations of metals. For example, the catalysts can be prepared by either precipitation or impregnation methods of the Cu, Ru, Cu—Pd, Ni—Cu, or Ni—Pd on a support as generally described in Satterfield on pp. 87-112 in *Heterogeneous Catalysts in Industrial Practice*, $2^{nd}$ ed. (McGraw-Hill, New York, 1991). The support is preferably inert, if not positively participative in the obtaining the desired result of the reaction, under the conditions of the reaction. The preferred support is carbon, which may be treated to enhance its support function for the catalyst loaded onto the carbon. One example of treatment is acid washing of the carbon.

When the catalyst is Cu—Pd or Ni—Pd, the Pd is preferably present in a minor amount as compared to the weight of the Cu or Ni. For, example, when the catalyst is Cu—Pd, the loading on the support in one embodiment is 0.1 to 20 wt % Cu and 0.1-1.0 wt % Pd. These same proportions can apply to the Ni—Pd catalyst. When the catalyst if Ni—Cu, the mole ratio of these metals can range from 1:99 to 99:1. In one embodiment, the molar ratio of these metals is about 1:1.

The foregoing description of catalysts applies to each of the hydrogenation reactions encompassed by the Hydrogenation Process and each of the hydrogenation reactions of the Intermediates Process, when these catalysts are used in the Intermediate Process.

Each of the reactant compounds HCFC-235cb, HCFC-225ca, HCFO-1224yd, and CFO-1214ya are commercially available or can be prepared by known processes in varying degrees of purity. Some impurities may participate in the hydrogenation reaction to form intermediates that can be converted directly or indirectly to the desired HFP propene. Other impurities may be unaffected by the reaction When the compound is $CF_3CF_2CHXCl$, wherein X is Cl, i.e. HCFC-225ca, the reaction product of the hydrogenation reaction in the presence of catalyst described above comprises the compound $CF_3CF=CH_2$ (HFO-1234yf).

This reaction product may also comprise at least one of the compounds $CF_3CF=CHCl$ (HCFO-1224yd) and $CF_3CF_2CH_2Cl$ (HCFC-235cb).

When the compound $CF_3CF=CHCl$ is in the reaction product, this compound can be converted to the compound $CF_3CF=CH_2$ by hydrogenation in the presence of a catalyst such as described above. The catalyst can be the same or different from the catalyst used to form the reaction product. The hydrogenation of the compound $CF_3CF=CHCl$ to a reaction product comprising $CF_3CF=CH_2$ is in effect practice of the present invention when the reactant compound is $CF_3CF=CXCl$, wherein X is H.

When the compound $CF_3CF_2CH_2Cl$ is in the reaction product, this compound can be converted to the compound $CF_3CF=CH_2$, first by dehydrofluorination of said compound $CF_3CF_2CH_2Cl$ to form the compound $CF_3CF=CHCl$ and then hydrogenation of said compound $CF_3CF=CHCl$ in the presence of catalyst as described above. Alternatively, the compound $CF_3CF_2CH_2Cl$ can be converted to $CF_3CF=CH_2$ by hydrogenation in the presence of catalyst as described above.

When the reactant compound comprises HCFC-225ca, this compound will typically be accompanied by the compound $CF_3CCl_2CHF_2$ (HCFC-225aa) in said contacting and reacting in the presence of the catalyst, whereby the reaction product will also comprise at least one of the compounds $CF_3CCl=CHF$ (HCFO-1224xe), $CF_3CHClCHF_2$ (HCFC-235da), $CF_3CH_2CF_2H$ (HCFC-245fa), and $CF_3CH=CHF$ (HFO-1234ze) as reaction products of the hydrogenation of the HCFC-225aa during the hydrogenation of the HCFC-225ca. The HCFO-1234xe and HFC-245fa are both intermediates for the formation of $CF_3CH=CHF$ (HFO-1234ze). The presence of HFO-1234ze in the reaction product means this compound is formed directly from the hydrogenation of HCFC-225aa.

When the reaction product compound is $CF_3CCl=CHF$ (HCFO-1234xe), this compound is hydrogenated in the presence of catalyst as described above to form a reaction product comprising at least one of the compounds $CF_3CH=CHF$ (HFO-1234ze) and $CF_3CHClCH_2F$ (HCFC-234db).

When the reaction product comprises the compound $CF_3CHClCH_2F$ (HCFC-234db), this compound is converted to the reaction product comprising the compound $CF_3CH=CHF$ by dehydrochlorination of the compound $CF_3CHClCH_2F$.

When the reaction product comprises the compound $CF_3CHClCHF_2$ (HCFC-235da) this compound is converted to reaction product comprising the compounds $CF_3CH=CF_2$ or $CF_3CH=CHF$. In one embodiment, the HCFC-235da can be dehydrochlorinated to form reaction product comprising HFO-1225zc ($CF_3CH=CF_2$). In another embodiment, the HCFC-235da is reacted with $H_2$ to remove both Cl and F (hydrodehalogenated) to form reaction product comprising HFO-1234ze.

When the reaction product comprises the compound $CF_3CH_2CF_2H$ (HCFC-245a), this compound can be dehydrofluorinated to form the reaction product comprising $CF_3CH=CHF$ (HFO-1234ze).

When the reactant compound is $CF_3CF_2CHXCl$, wherein X is H, i.e. (HCFC-235cb), the reaction product with $H_2$ comprises the compound $CF_3CF=CH_2$ (HFO-1234yf).

When the reactant compound is $CF_3CF=CXCl$, wherein X is Cl or $CF_3CF=CXCl$, wherein X is H, or a mixture of these reactant compounds, the reaction product of the hydrogenation reaction in the presence of catalyst as described above comprises the compound $CF_3CF=CH_2$. Thus, CFO-1214ya or HCFO 1224yd can be the reactant compounds, one without the other, or these compounds can be present as a mixture of reactant compounds.

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed provided that these additional included materials, steps, features, components, or elements do materially affect the basic and novel characteristic(s) of the claimed invention, especially the mode of action to achieve the desired result of any of the processes of the present invention. The term 'consisting essentially of' occupies a middle ground between "comprising" and 'consisting of'.

Where applicants have defined an invention or a portion thereof with an open-ended term such as "comprising," it should be readily understood that (unless otherwise stated) the description should be interpreted to also include such an invention using the terms "consisting essentially of" or "consisting of."

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

EXAMPLES

The concepts described herein will be further described in the following Examples, which do not limit the scope of the invention as described in the claims.

Example 1—Hydrogenation of 225ca to 1234y, 1224yd, and 235cb 10 cc 10% Cu/C is loaded into a ½ inch (1.3 cm) Hastelloy® C 227 reactor. The catalyst is reduced at 250° C. with $H_2$ for 4 hours. Then HCFC-225ca (GC analysis of HCFC-225ca reactant mixture in Table 1), is fed at 3.11 sccm with $H_2$ (10.5 sccm) at 325° C. and 350° C. at atmosphere pressure. The reaction product stream from the reactor is analyzed by GC and GC-MS. The result of the hydrogenation reaction is shown in Table 2. HFO-1234yf, HCFO-1224yd and HCFC-235cb are reaction products made in this reaction.

TABLE 1

| GC analysis of starting material 225ca mixture | | | | | |
|---|---|---|---|---|---|
| Compound | 235cb | 225ca | 225aa | 225cb | Others |
| Mol % | 1.44 | 83.25 | 4.14 | 11.14 | 0.03 |

TABLE 2

| GC analysis of reaction product | | | | | | | | | |
|---|---|---|---|---|---|---|---|---|---|
| | | | mol % of product | | | | | | |
| Temp ° C. | Organic SCCM | $H_2$ sccm | 1234yf | 1224yd | 1224xe | 235cb | 225ca | 225aa | 225cb |
| 325 | 3.11 | 10.5 | 1.51 | 1.82 | 2.07 | 3.58 | 73.87 | 1.35 | 11.52 |
| 350 | 3.11 | 10.5 | 4.71 | 6.77 | 2.48 | 10.66 | 49.0. | ND | 12.66 |

Example 2—Hydrogenation of HCFC-225ca, Cu—Pd Catalyst 10 cc 0.5% Pd-8.5% % Cu/C is loaded into a ½ inch (1.3 cm) Hastelloy® C 227 reactor. The catalyst is reduced at 400° C. with $H_2$ for 4 hours. Then a 225ca/cb mixture (GC analysis of HCFC-225ca reactant mixture in Table 1), is fed at 3.11 sccm with $H_2$ (10.5 sccm) at 125, 140 and 160° C. at atmosphere pressure. The stream from the reactor is analyzed by GC and GC-MS. The result of the test is shown in Table 3. HFO-1234yf, CFO-1224yd and HCFC-235cb are made in this reaction.

TABLE 3

| GC analysis of reaction product | | | | | | | |
|---|---|---|---|---|---|---|---|
| Temp | mol % of product | | | | | | |
| ° C. | 1234yf | 1224yd | 1224xe | 235cb | 225ca | 225aa | 225cb |
| 125 | 0.19 | 14.49 | 3.30 | 16.03 | 51.03 | 0.95 | 12.80 |
| 140 | 0.38 | 29.17 | 3.44 | 34.29 | 17.39 | 0.82 | 12.56 |
| 160 | 0.73 | 36.64 | 3.44 | 41.11 | 1.41 | ND | 12.5 |

This Example shows the conversion of 225ca and 1224yd to 1234yf in that the 1224yd is an intermediate to the formation of 1234yf.

Example 3—Hydrogenation of HCFC-235cb to HFO-1234yf 10 cc 10% Cu/C is loaded into a ½ inch (1.3 cm) Hastelloy® C 227 reactor. The catalyst is reduced at 250° C. with $H_2$ for 4 hours. Then the 235cb was fed at 3.5 sccm with $H_2$ (6 sccm) at 325 C and 350 C at atmosphere pressure. The stream from the reactor is analyzed by GC and GC-MS. The result of the test is shown in Table 4. The 235cb is converted to 1234yf at a selectivity of 88 to 90%.

TABLE 4

| GC analysis of reaction product | | | |
|---|---|---|---|
| Temp | mol % of product | | |
| ° C. | 1234yf | 245cb | 235cb |
| 325 | 14.85 | 1.89 | 82.98 |
| 350 | 26.69 | 2.71 | 69.11 |

Example 4—Hydrogenation of 225ca to 1234y, 1224yd and 235cb, Ni—Cu Catalyst 10 cc Johnson Matthey CP447 Ni—Cu/C is loaded into a ½ inch (1.3 cm) Hastelloy® C 227 reactor. The catalyst is reduced at 400° C. with $H_2$ for 4 hours. Then 225ca (GC analysis of mixture in Table 5), is fed at 3.11 sccm with $H_2$ (11 sccm) at 225, 250, 275 and 300 C at atmosphere pressure. The stream from the reactor is analyzed by GC and GC-MS.

The result of the test is shown in Table 6. The 1234yf, 1224yd and 235cb are made in this reaction.

TABLE 5

| GC analysis starting 225ca mixture Mole Percent | | | |
|---|---|---|---|
| 225ca | 225aa | 225cb | Others |
| 47.43% | 3.09% | 48.53% | 0.95% |

TABLE 6

GC analysis of reaction product (F22E is CF$_3$CF$_2$CH=CHCF$_2$CF$_3$)

| Temp °C. | 1234yf | 1234ze | F22E | 1224yd-E | 1224 isomer 1 | 235cb | 1224 isomer 2 | 225ca | 225aa | 225cb | Others |
|---|---|---|---|---|---|---|---|---|---|---|---|
| 225 | 2.81% | 0.00% | 0.00% | 0.85% | 0.36% | 0.35% | 0.11% | 40.53% | 2.90% | 50.94% | 1.16% |
| 250 | 4.92% | 0.00% | 0.08% | 1.72% | 0.60% | 0.74% | 0.23% | 35.32% | 2.53% | 50.92% | 2.94% |
| 275 | 8.56% | 0.00% | 0.38% | 3.44% | 1.12% | 1.77% | 0.44% | 25.42% | 1.87% | 52.53% | 4.46% |
| 300 | 11.66% | 0.16% | 1.40% | 5.82% | 1.53% | 3.39% | 0.70% | 13.63% | 1.13% | 54.30% | 6.27% |

Example 5—Hydrogenation of 1214ya to 1234y and 1224yd, Ni—Cu Catalyst 10 cc Johnson Matthey CP447 Ni—Cu/C is loaded into a ½ inch (1.3 cm) Hastelloy® C 227 reactor. The catalyst is reduced at 400° C. with H$_2$ for 4 hours. Then 1214ya is fed at 3.11 sccm with H$_2$ (11 sccm) at 225, 250, 275 and 300° C. at atmosphere pressure. The stream from the reactor is analyzed by GC and GC-MS. 1234yf and 1224yd are made in this reaction as shown in Table 7.

TABLE 7

GC analysis of reaction product

| Temp °C. | 1234yf | 1224yd | 1214ya | Others |
|---|---|---|---|---|
| 225 | 2% | 1% | 95% | 2% |
| 250 | 18% | 6% | 70% | 6% |
| 275 | 23% | 18% | 50% | 9% |
| 300 | 45% | 23% | 25% | 7% |

Example 6—Hydrogenation of 1214ya to 1234yf and 1224yd, Pd—Cu Catalyst 10 cc 0.5% Pd-8.5% % Cu/C is loaded into a ½ inch (1.3 cm) Hastelloy® C 227 reactor. The catalyst is reduced at 400° C. with H$_2$ for 4 hours. Then 1214ya is fed at 3.11 sccm with H$_2$ (10.5 sccm) at 125, 140 and 160° C. at atmosphere pressure. The stream from the reactor is analyzed by GC and GC-MS. The 1234yf and 1224yd are made as shown in Table 8.

TABLE 8

GC analysis of reaction product

| Temp °C. | mol % of product | | | |
| | 1234yf | 1224yd | 1214ya | Others |
|---|---|---|---|---|
| 125 | 0.6% | 20% | 69.4% | 10% |
| 140 | 1.2% | 40% | 38.8% | 20% |
| 160 | 3% | 60% | 12% | 25% |

What is claimed is:

1. A composition comprising a reaction product and at least one intermediate convertible to the reaction product wherein the reaction product comprises CF$_3$CF=CH$_2$ and CF$_3$CH=CHF, and the intermediate comprises CF$_3$CF$_2$CH$_2$Cl.

2. The composition of claim 1 wherein the intermediate further comprises CF$_3$CF=CHCl.

3. The composition of claim 1 further comprising CF$_3$CF$_2$CHCl$_2$.

4. The composition of claim 1 wherein the composition consists essentially of intermediates that are convertible to the reaction product.

5. A composition consisting essentially of CF3CF=CH2, CF3CH=CHF and CF$_3$CF$_2$CH$_2$Cl.

* * * * *